United States Patent [19]
Eury et al.

[11] Patent Number: 5,316,774
[45] Date of Patent: May 31, 1994

[54] BLOCKED POLYMERIC PARTICLES HAVING INTERNAL PORE NETWORKS FOR DELIVERING ACTIVE SUBSTANCES TO SELECTED ENVIRONMENTS

[75] Inventors: Robert P. Eury, Half Moon Bay; Rajesh Patel, San Mateo, both of Calif.

[73] Assignee: Advanced Polymer Systems, Inc., Redwood City, Calif.

[21] Appl. No.: 806,860

[22] Filed: Dec. 9, 1991

Related U.S. Application Data

[63] Continuation of Ser. No. 541,111, Jun. 20, 1990, abandoned.

[51] Int. Cl.$^5$ .......................... A61K 9/14; A61K 9/10; A61K 47/32; A61K 47/38
[52] U.S. Cl. ........................... 424/501; 424/499; 424/426; 424/428; 514/951
[58] Field of Search .................. 424/78, 81, 499, 501, 424/426, 428; 514/964, 965, 722.4, 772.6

[56] References Cited

U.S. PATENT DOCUMENTS

| | | | |
|---|---|---|---|
| 3,991,017 | 11/1976 | Barrett et al. | 260/2.1 R |
| 4,221,871 | 9/1980 | Meitzner et al. | 521/29 |
| 4,575,539 | 3/1986 | DeCrosta et al. | 524/458 |
| 4,690,825 | 9/1987 | Won | 424/501 |
| 4,692,462 | 9/1987 | Banerjee | 514/449 |
| 4,806,360 | 2/1989 | Leong et al. | 424/487 |
| 4,963,369 | 10/1990 | Song et al. | 426/5 |

FOREIGN PATENT DOCUMENTS

| | | |
|---|---|---|
| 0171528 | 2/1986 | European Pat. Off. |
| 0194838 | 9/1986 | European Pat. Off. |
| 0225615 | 6/1987 | European Pat. Off. |
| 0301133 | 2/1989 | European Pat. Off. |
| 0306236 | 3/1989 | European Pat. Off. |
| 872554 | 4/1987 | South Africa |
| 2017113 | 10/1979 | United Kingdom |

*Primary Examiner*—Edward Webman
*Attorney, Agent, or Firm*—Townsend and Townsend Khourie and Crew

[57] ABSTRACT

A composition for the controlled release of an active substance comprises a polymeric particle matrix, where each particle defines a network of internal pores. The active substance is entrapped within the pore network together with a blocking agent having physical and chemical characteristics selected to modify the release rate of the active substance from the internal pore network. In an exemplary embodiment, drugs may be selectively delivered to the intestines using an enteric material as the blocking agent. The enteric material remains intact in the stomach but will degrade under the pH conditions of the intestines. In another exemplary embodiment, the sustained release formulation employs a blocking agent which remains stable under the expected conditions of the environment to which the active substance is to be released.

51 Claims, 1 Drawing Sheet

BLOCKED POLYMERIC PARTICLES HAVING INTERNAL PORE NETWORKS FOR DELIVERING ACTIVE SUBSTANCES TO SELECTED ENVIRONMENTS

This is a continuation of Ser. No. 07/541,111, filed Jun. 20, 1990.

The subject matter of the present application is related to that of copending application Ser. No. 07/355,718, filed on May 22, 1989, the disclosure of which is incorporated herein by reference.

BACKGROUND OF THE INVENTION

Field of the Invention

The present invention relates generally to compositions and methods for the controlled release of an active substance and, in particular, to the use of porous particles having the active substance entrapped therein where the release rate of the substance is modified by the presence of a blocking agent in the pores.

Compositions and methods for the release of an active substance, such as a drug, from a reservoir over time are known, and numerous specific approaches exist to achieve such controlled release. Two widely practiced approaches are of particular interest to the present invention. In the first such approach, a solid core of an active substance is encapsulated in a sustained release coating. The sustained release coating is usually a permeable membrane material which remains intact as the drug diffuses therethrough at a desired rate. Such sustained release coatings are very useful for controlling the release rate of many substances, but are much less useful with soluble and low viscosity substances. Moreover, the release rate is generally not responsive to various environmental conditions, such as pH, ionic strength, and the like.

In the second approach, drugs or other active substances are encapsulated or coated with a material which dissolves or degrades in response to a change in environmental conditions. For example, pH-responsive coatings (referred to as enteric coatings) may be provided on drugs to protect the drug in the low pH environment of the stomach but dissolve when the pH rises as the drug passes to the intestines. Such coatings include cellulose acetate phthalate, polyvinyl acetate phthalate, hydroxypropylcellulose phthalate, methylcellulose phthalate, and the like. Although these coatings are very effective in protecting drugs in the stomach, they do not generally provide a controlled release rate once the drug reaches the intestines.

A less widely employed delivery approach utilizes porous polymeric particles for absorbing and releasing drugs and other active substances at a controlled release rate. See, e.g., U.S. Pat. No. 4,692,462, discussed below. In such systems, the diffusion rate of the drug or other active substance through the pores determines the release rate. The diffusion rate, of course, depends on pore size, drug viscosity, temperature, and the like. In the case of drug delivery, drugs absorbed in porous polymeric particles are usually combined in an adhesive or other matrix material as part of a transdermal drug delivery system. In another example, drugs have been adsorbed onto porous resin beads which are then coated with a membrane diffusion barrier, e.g., ethylcellulose, in order to effect sustained release. See, European patent application 171 528, discussed below.

One difficulty with all of these delivery systems has been modifying the system release characteristics in order to achieve a desired release rate for particular active substance. The physical characteristics of drugs and other active substances may vary widely, including changes in viscosity, charge characteristics, molecular weight, and the like, and the release rate in any delivery system may vary widely depending on the nature of the substance which is being delivered. This problem is particularly evident when employing porous particle delivery systems where modification of the pore characteristics can be achieved only within certain limitations.

Thus it would be desirable to provide compositions and methods for the delivery of drugs and other active substances. It would be particularly desirable if the compositions could be readily modified to achieve a desired release rate for active substances having a wide variety of physical and chemical characteristics. It would be further desirable if the compositions could be modified to control the release rate of such divergent active substances under a variety of different external conditions, such as pH, temperature, ionic strength, and the like.

Description of the Background Art

U.S. Pat. No. 4,690,825, describes the topical delivery of various active substances using porous polymeric particles having the substances absorbed therein. U.S. Pat. No. 4,692,462, discloses the use of charged ion exchange resins for containing drugs within a transdermal delivery system. U.S. Pat. No. 4,221,778; South African patent application 87/2554; and European patent application 171 528, describe compositions comprising ion exchange resin particles having a drug adsorbed thereon, where the particles are coated with a diffusion membrane such as ethyl cellulose. European patent application 225 615, describes the release of dextromethorphan from cross-linked polystyrene sulfonate resin particles. U.S. Pat. No. 3,991,017, describes hybrid ion exchange resin where the macropores of the resin are at least partly filled with a copolymer gel. U.S. Pat. No. 4,575,539, describes the use of hydrogel bead for drug delivery, where the beads are swelled with an acrylic swelling agent.

SUMMARY OF THE INVENTION

Compositions according to the present invention comprise polymeric particles each defining a network of internal pores optionally present in a vehicle intended for topical or other delivery. An active substance, such as a drug, is entrapped within the internal pore network together with a blocking agent having physical and chemical characteristics selected to modify the release rate of the active substance. The active substance is usually a solid which is soluble in a vehicle or other environment, where the blocking agent inhibits premature release of the agent into the vehicle or environment. The active substance may also be a liquid, gel, semi-solid, or the like which in the absence of the blocking agent would be released from the polymeric particles at a greater than desired rate. The blocking agent is usually a linear or cross-linked polymeric material which reduces or otherwise modifies the release rate of the active substance. In a particular embodiment, the blocking agent is degradable under preselected external conditions, such as pH, ionic strength, temperature, or the like.

According to the method of the present invention, compositions as just described may be prepared by introducing in a predetermined order (a) the active substance and (b) the blocking agent having preselected physical and chemical characteristics to the porous polymeric particles. Usually, the active substance will be introduced first, although in some cases it may be desirable to introduce the blocking agent first or to introduce the active substance and the blocking agent substantially simultaneously. The blocking agent will usually itself be a polymeric material and may be introduced either as a preformed linear polymer or as a linear or cross-linked polymer which is polymerized in situ within the internal pore network.

In the exemplary embodiments, the blocking agent is a cross-linked hydrogel polymer produced by in situ polymerization of the corresponding monomers. It has been found that such particles have the release characteristics of a hydrogel bead having an apparent diameter larger than the actual diameter due to the added tortuosity of the internal pore network.

The polymeric particles of the present invention may be incorporated in a wide variety of product formulations, particularly including formulations for topical or oral delivery of drugs and other active substances. For topical delivery, the blocking agent will usually be selected to provide a substantially constant inhibition of diffusion of active substance from the particles when the formulation is applied to the skin. Numerous carrier and vehicle solutions are available for such topical delivery, including lotions, creams, ointments, and the like. For oral delivery, the blocking agent will typically be pH-sensitive. By storing the beads in a suitable carrier vehicle at a first pH, the drug or other active substance can then be delivered to an environment at a second pH, such as the mouth, stomach, intestines, and the like. The blocking agent will be selected to degrade at the second pH, allowing release of the active substance from the polymeric particles.

DESCRIPTION OF THE PREFERRED EMBODIMENTS

Figure 1:
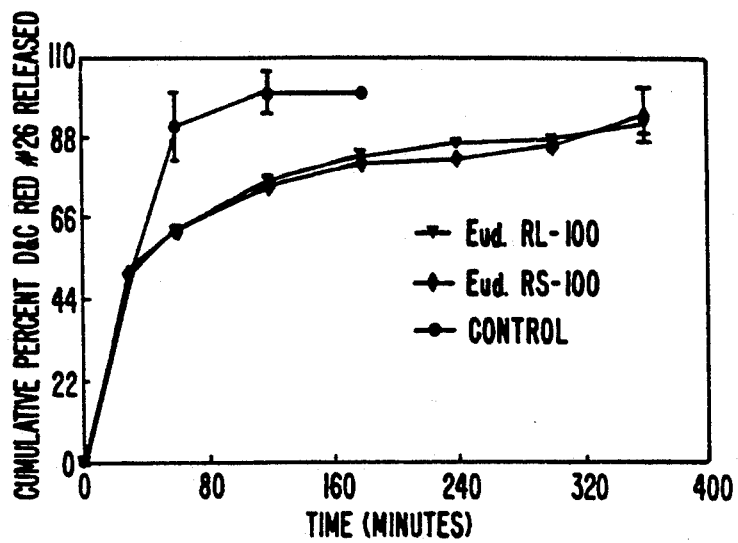
FIG. 1 is a graph which compares the release rate of a dye from polymeric particles blocked with Eudragit compounds with the release rate from non-blocked particles.

The compositions of the present invention comprise an active substance entrapped in an internal pore network of a polymeric bead delivery system. The active substance is intended to be released by diffusion from the internal pore network for controlled delivery of the substance to an environment, either in vivo or in vitro. By co-entrapping a suitable blocking agent within the internal pore network, the diffusion characteristics of the active substance from the pore network may be modified in some desirable manner. For example, the use of a non-degradable blocking agent (i.e., one which is stable within the environment to which it is subsequently introduced) will inhibit diffusion and prolong release of the active substance by a constant factor during the entire release period. Alternately, by selecting a blocking agent which is degradable when exposed to a preselected environment, the release characteristics may be selected to change during the release, usually by enhancing or inhibiting the release of the active substance over time.

The present invention can be used to entrap and deliver a wide variety of active substances, including virtually any compound, mixture, suspension, solution, dispersion, or the like, which may be introduced into a porous network defined within carrier beads, as described more fully hereinbelow. The molecular weight of the active substance is not critical, with molecular weights in the range from about 600 to $10^6$ daltons, more usually in the range from about $10^3$ to $2 \times 10^5$ daltons, finding the greatest use. The active substance will usually be a solid which is soluble in an environment in which the bead is to be stored, e.g., a liquid carrier or vehicle, but may also be liquid, gel, semi-solid, or the like, where it is desired to inhibit or otherwise control the release rate from the polymeric particles. In the case of solid or semi-solid active substances, it will usually be desirable to dissolve the substances in a suitable solvent to facilitate introduction and release of the substances from the polymeric particles. Usually, only a single active substance will be present within the internal porous network, but under certain circumstances it may be desirable to introduce two or more compatible active substances when the desired release rates can be controlled using the same blocking agent. In other cases, it may be desirable to use two or more different blocking agents in order to achieve particular release rate profiles over time.

Most often, the compositions of the present invention will be used to deliver an active substance to a human or other animal for purposes of therapy, hygiene, analgesics, cosmetics, or the like. For such purposes, the compositions may be delivered topically, orally, intravascularly, intraocularly, intraperitoneally, and the like. Such uses where the compositions are delivered to a human or other animal will generally be referred to as in vivo uses. The compositions of the present invention will also have in vitro uses where an active substance is being delivered to an environment or system other than a human or animal. Exemplary in vitro uses include denture cleaning agents, contact lens care compositions, cleansers, air fresheners, and the like. For both in vivo and in vitro uses, the compositions will deliver the active substance to a surrounding environment where the release rate to the environment is controlled or modulated at least in part by the presence of one or more blocking agents within the internal pore network defined by the polymeric particles.

One of the major in vivo uses for the compositions of the present invention will be for the delivery of drugs and other pharmaceutical agents in human and veterinary applications. Exemplary drugs which may be delivered by the system of the present invention include analgesics, anesthetics, anthelmintics, antidotes, antiemitics, antihistamines, antimalarials, antimicrobials, antipyretics, antiseptics, antituberculotics, antitussives, antivirals, cardioactive drugs, cathartics, chemotherapeutic agents, corticoids (steroids), depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasoconstrictors, vasodilators, vitamins, xanthine derivatives, and the like.

The present invention is particularly useful for the oral delivery of drugs which are to be released in the intestines rather than in the stomach. Such drugs include antibiotics, vitamins, non-steroidal anti-inflammatory substances, and the like. As discussed in more detail hereinbelow, in such cases the blocking agent will be selected to remain intact during storage and while the composition passes through the stomach. On exposure to the higher pH environment of the intestines, however, the blocking agent will decompose thus releasing the drug from the internal pore network of the carrier particles.

The compositions of the present invention will also find use with orally-delivered active substances other than drugs. For example, the compositions are particularly suitable for delivering anti-plaque agents, such as polyphosphates, and anti-tartar agents, such as chlorohexidine gluconate, when incorporated in toothpastes, mouthwashes, and other oral hygiene products. The compositions will also be useful for delivering flavoring agents, as described in detail in copending application Ser. No. 07/435,100, the disclosure of which is incorporated herein by reference.

Active substances for topical delivery which may be incorporated in the compositions of the present invention include emollients, sunscreens, insect repellents, fragrances, anti-acne substances (e.g., benzoyl peroxide), corticosteroids, antimicrobials, antiperspirants, and the like. General considerations concerning the topical delivery of such active substances are described in U.S. Pat. No. 4,690,825 and copending application Ser. No. 07/091,641, the disclosures of which are incorporated herein by reference.

A wide variety of materials suitable for the blocking agent are available. Such materials should be compatible and non-reactive with the active substance(s) as well as having physical and chemical characteristics selected to block, inhibit, or otherwise modify the release rate of the active substance(s) from the internal pore network of the carrier particles. Normally, the blocking agent will function by physically blocking at least a portion of the pore network in order to inhibit passage of the active substances. Optionally, the physical and chemical properties of the blocking agent may be modified when the polymeric carrier particles are placed in a different environment, typically being responsive to changes in pH, ionic strength, the presence of enzymes, temperature, the nature of the solvent, bacterial degradation, and the like.

The blocking agent will usually be a polymeric material, more usually being a linear or cross-linked organic polymer, as described in more detail hereinbelow. Linear polymers may be pre-formed and introduced to the internal pore network of the carrier particles, e.g., by absorption. Alternatively, linear and cross-linked polymers may be formed in situ within the internal pore network by the absorption of suitable monomers and the subsequent initiation of polymerization.

Of particular interest to the present invention are enteric blocking agents which remain intact in the stomach (i.e., are gastroresistant) but will degrade in the intestines (i.e., are enterosoluble). Materials suitable as enteric blocking agents will remain intact in the low pH environment of the stomach, but will solubilize at the higher pH environment of the intestines. A variety of suitable materials are known in the art, particularly as coatings for solid core drug formulations. The most effective enteric materials are polyacids having a $pK_a$ of from about 3 to 5. Exemplary materials include fat-fatty acid mixtures, ethyl cellulose, cellulose acetate phthalates, and the like.

Also suitable as enteric coatings are various poly(meth)acrylates which may be introduced to the polymeric carrier particles either by in situ polymerization or by absorption of an aqueous dispersion of the materials. Suitable poly(meth)acrylates include copolymers of methylmethacrylate and ethylacrylate as ester components with methacrylic acid which contain carboxylic groups that are transformed to carboxylate groups at a pH of from about 5 to 7. They are thus able to form water-insoluble materials which are resistant to gastric juices and methacrylate ester copolymers which are insoluble over the entire physiological pH range. Specific copolymers useful as enteric materials are as follows.

| Enteric Material | Molecular Weight | Preferred Monomer Ratio |
|---|---|---|
| poly (methacrylic acid, ethylacrylate) copolymer | 250 kD | 1:1 |
| poly (methacrylic acid, methylmethacrylate) copolymer | 135 kD | 1:2 to 1:2 |
| poly (ethylacrylate, methylmethacrylate) copolymer | 800 kD | 2:1 |
| poly (ethylacrylate, methacrylate) trimethyl-ammoniumethylmethacrylate chloride | 150 kD | 1:2:0:2 |
| poly (ethylacrylate, methylmethacrylate) trimethylammoniumethylmethacrylate chloride | 150 kD | 1:2:0:2 |

Polymeric particles useful in the present invention each define a network of internal pores which contain he active substance and blocking agent. The nature of the particles is not critical, with rigid and elastic spherical and non-spherical, non-degradable and erodible, and open- and closed-pore particles all being suitable. In the exemplary embodiment, the polymeric particles are substantially non-collapsible beads having a cross-linking density of at least about 10%, more usually in the range from about 20% to 80%. The average bead diameter will range from about 5 μm to 100 μm, usually in the range from about 10 μm to 40 μm.

Conveniently, polymeric beads useful in the present invention may be formed by suspension polymerization of suitable monomers in an immiscible phase including a porogen. Generally, the monomers and the porogen are first mixed together, and the resulting mixture then suspended in the immiscible phase, usually an aqueous phase. The immiscible phase is then agitated to form droplets of the monomer mixture, and polymerization of the monomer mixture is initiated to form the desired beads. Once the beads are formed, the porogen may be extracted and the active substance and blocking agent introduced in a predetermined order, with the active substance typically being introduced by absorption and the blocking substance being introduced by absorption or, in the case of polymeric blocking agents, by in situ polymerization where the monomers have been introduced by absorption. In some cases, however, it will be possible to utilize the active substance and/or blocking agent as the porogen (or to combine the active substance and/or blocking agent with a suitable porogen) so that the product of suspension polymerization may be used directly without extraction. The resulting beads are a dry powder which may be incorporated directly into a desired final product, usually by conventional mixing techniques.

The polymeric particles may be rigid or elastic, spherical or non-spherical and non-degradable or erodible. The preparation of rigid beads is described in detail below, while the preparation of elastic particles (hydrogels) is described in numerous references, such as Kirk-Othmer, *Encyclopedia of Chemical Technology*, 3rd Ed., John Wiley & Sons, Vol. 15, pp. 656-675 (1981), and U.S. Pat. Nos. 4,058,491; 4,060,678; and 4,071,508. Most particle preparation processes will result in the formulation of spherical beads, but beads having non-spherical asymmetric, and/or irregular geometries will also find use so long as they meet the necessary physical parameters set forth below.

Suitable polymeric particles will not readily undergo unwanted reactions, will be stable over a wide pH range, and will resist moderate oxidation and reduction. The particles should be stable at higher temperatures and have a relatively long shelf life. Desirable physical parameters for the polymeric particles are as follows:

|  | Broad Range | Preferred Range |
| --- | --- | --- |
| Particle Size | 5-100 μm | 10-40 μm |
| Particle Density | 0.4-2.0 g/cc | 0.6-1.5 g/cc |
| Pore Volume | 0.1-2.0 cc/g | 0.3-1.0 cc/g |
| Pore Diameter | 0.001-3 μm | 0.003-1 μm |
| Surface Area | 1-500 m$^2$/g | 20-200 m$^2$/g |

The particles may be formed from a wide variety of polymers, including natural polymers such as carboxylmethylcellulose, cellulose acetate phthalate, ethylcellulose, methylcellulose, arabinogalactan, nitrocellulose, hydroxypropylcellulose, and succinylated gelatin; and synthetic polymers such as polyvinyl alcohol, polyethylene, polypropylene, polystyrene, polyacrylamide, polyether, polyester, polyamide, polyurea, epoxy, ethylene vinyl acetate copolymer, polyvinylidene chloride, polyvinyl chloride, polyacrylate, polyacrylonitrile, chlorinated polyethylene, acetal copolymer, polyurethane, polyvinyl pyrrolidone, poly(p-xylene), polymethylmethacrylate, polyvinyl acetate, and polyhydroxyethyl methacrylate.

The preferred polymer particle matrix of the present invention comprises rigid polymeric beads having a substantially non-collapsible pore structure. That is, the beads will substantially retain their internal pore structure even after the porogen (used in formation of the bead as described hereinafter) has been extracted and the pores are empty. Such beads are mechanically stable compared with non-rigid materials, allowing manufacturing, processing, and handling of the beads under relatively rigorous conditions which might result in the rupture or damage of less stable materials. More importantly, the non-collapsible pores facilitate introduction of the active substance and blocking agent, as described in more detail hereinafter.

The rigid polymeric beads of the present invention are formed by polymerization and cross-linking of one or more preselected monomers to form a molecular structure having a substantially non-collapsible network of pores resulting from the presence of the porogen during polymerization. At least one monomer will be polyethylenically unsaturated, and usually the polymer will include a monoethylenically unsaturated co-monomer. The degree of cross-linking may then be controlled by adjusting the ratio of monoethylenically unsaturated monomer to polyethylenically unsaturated monomer, as discussed in more detail hereinbelow. The active substance and blocking agent are entrapped within the network of pores, and the resulting loaded particles act to release the active substance into a desired environment at a preselected rate, depending on the physical characteristics of the particles as well as those of the blocking agent.

The rigid polymer beads of the present invention will have greater than 10% cross-linking, usually having in the range from about 20% to 80% cross-linking, more usually having in the range from about 25% to 60% cross-linking, and typically being in the range from about 45% to 55% cross-linking. The calculated or theoretical percentage of cross-linking is defined as the weight of polyethylenically unsaturated monomer (or monomers) divided by the total weight of monomer, including both polyethylenically unsaturated and monoethylenically unsaturated monomers.

The beads of the preferred polymer are conveniently formed by suspension polymerization in a liquid-liquid system. In general, a solution containing monomers, a polymerization catalyst (if used), and an inert but fully miscible liquid porogen is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid porogen has accordingly served as a "pore-forming agent" and occupies the pores of the formed beads.

Materials suitable as porogens will be liquid substances which meet the following criteria:

1. They are either fully miscible with the monomer mixture or capable of being made fully miscible by the addition of a minor amount of non-water-miscible solvent;
2. They are immiscible with water, or at most only slightly soluble;
3. They are inert with respect to the monomers, and stable when in contact with any polymerization catalyst used and when subjected to any conditions needed to induce polymerization (such as temperature and radiation); and
4. They are readily extracted from the pore network of the beads once polymerization is complete.

Suitable porogens include a wide range of substances, notably inert, non-polar organic solvents. Some of the most convenient examples are alkanes, cycloalkanes, and aromatics. Specific examples of such solvents are alkanes of from 5 to 12 carbon atoms, straight or branched chain cycloalkanes of from 5 to 8 carbon atoms, benzene, and alkyl-substituted benzenes, such as toluene and the xylenes. Extraction of the porogen may be effected by solvent extraction, evaporation, or similar conventional operations. The porogen extraction step accomplishes the removal of unwanted species from the polymerized structures prior to impregnation with the desired active substance and blocking agent. Such unwanted species include unreacted monomers, residual catalysts, and surface active agents and/or dispersants remaining on the bead surfaces.

Extraction of the porogen may be effected in a variety of ways, depending on the chemical nature of the porogen and its behavior in combination with that of the other species present. For example, the beads may be recovered from the suspension by filtration, preferably using vacuum apparatus (such as a Beuchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

The polymerization process used in preparing the beads of the polymer delivery system can be modified to control both the porosity and the particle diameter of the beads. Particle diameter is controlled primarily by the degree of agitation, with more rigorous agitation causing smaller droplets and hence smaller polymerized beads. The pore diameter and pore volume, in contrast, are controlled primarily by the cross-linking density. Porosity is increased by increasing the amount of cross-linking monomer used, or by increasing the porogen concentration in the monomer mixture, or both. An increase in porosity increases the surface area of the bead and hence the weight percent of the active ingredient or substance which may be held within the bead. Bead diameter is also affected by the concentration of dispersing agent in the immiscible phase.

The bead diameter in the polymer delivery system should be in the range from about 5 to 100 microns. Beads having an average diameter in the range from about 5 microns to no more than about 70 microns are preferred, with a bead diameter in the range from about 10 microns to about 40 microns being particularly preferred.

The pore dimensions within the beads may vary widely, with optimum dimensions depending on the chemical characteristics of the polymers used as well as the diffusive characteristics of the active substance and intended effect of the blocking agent. Different systems will thus call for different optimum ranges of pore volume distribution to obtain the most desirable properties for the overall formulation. In general, however, best results are obtained with total pore volumes ranging from about 0.1 to about 2.0 cc/g, preferably from about 0.3 to about 1.0 cc/g; pore surface areas ranging from about 1 to about 500 m$^2$/g, preferably from about 20 to about 200 m$^2$/g; and average pore diameters ranging from about 0.001 to about 3.0 microns, preferably from about 0.003 to about 1.0 micron. Following conventional methods of measuring and expressing pore sizes, the pore diameters are measured by techniques such as nitrogen or mercury porosimetry and are based on the model of a pore of cylindrical shape.

In order to form the cross-linked polymer beads of the present invention, it is necessary to polymerize either polyethylenically unsaturated monomers, i.e., those having at least two sites of unsaturation, or to polymerize monoethylenically unsaturated monomers in the presence of one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers suitable for preparing polymer beads for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The particularly preferred polymer delivery system of the present invention is formed by the copolymerization of methylmethacrylate and ethylene glycol dimethylmethacrylate. Usually, the methylmethacrylate will be present at from about 10 to 80 percent of the monomer mixture, more usually at about 20 to 60 percent of the monomer mixture, typically being in the range from about 45 to 55 percent of the monomer mixture, with the ethylene glycol dimethylmethacrylate forming the remainder of the mixture.

The polymer particle compositions of the present invention may be utilized by themselves in the form of a dry powder but will more usually be incorporated into a liquid or solid vehicle or carrier selected to facilitate the intended type of delivery or administration. Such vehicles or carriers may optionally include solvents, thickeners, preservatives, or other components as well known in the art to complete a desired dosage or delivery form.

For oral drug delivery, the polymeric particles carrying the drug may be incorporated into a variety of known dosage forms, as described in, for example, Remington's Pharmaceutical Sciences, Mack Publishing Company, Easton, Pa. 16th Ed., 1982, the disclosure of which is incorporated herein by reference. The composition or formulation to be administered will contain a preselected quantity of the active substance(s) contained within the polymeric particles which are dispersed therein. Usually, a pharmaceutically-acceptable non-toxic dosage form is prepared using conventional excipients, such as pharmaceutical grades of mannitol, lactose, starch, magnesium stearate, sodium saccharin, talcum, cellulose, glucose, sucrose, magnesium, carbonate, and the like. Such compositions may be in the form of solutions, suspensions, tablets, pills, capsules, powders, and the like.

For parenteral administration, including both intravascular and intramuscular administration, the polymeric particles of the present invention will normally be suspended in an injectable water or saline carrier. Such formulations are well known in the art.

For topical delivery, the polymeric carrier particles of the present invention may be incorporated in a variety of creams, lotions, ointments, cosmetic bases, alcohol bases, and the like. The incorporation of the polymeric particles into vehicles and carriers for topical delivery is well described in U.S. Pat. No. 4,690,825 and copending application Ser. No. 07/091,641, the disclosures of which have previously been incorporated herein by reference.

Methods for incorporating the polymeric particles of the present invention into transdermal drug delivery systems are well described in copending application Ser. No. 07/355,718, the disclosure of which is incorporated herein by reference.

Methods for incorporating the polymeric particles of the present invention having entrapped flavoring agents are well described in copending application Ser. No. 07/435,100, the disclosure of which is incorporated herein by reference.

For ophthalmic administration, the polymeric particles of the present invention will usually be incorporated into a liquid carrier which is isotonic with the ocular environment and which includes suitable buffering agents and preservatives. Lacrimal fluid having an isotonicity equal to that of an 0.9% sodium chloride solution is particularly suitable, although other solutions having isotonicity in the range from about 0.6% sodium chloride to about 2.0% sodium chloride may also find use. In some cases, it may be desirable to provide hypertonic carrier solutions in order to enhance absorption. Boric acid vehicles having a pH slightly below 5 may also be used, as can phosphate buffer systems having adjusted isotonicity.

In addition to the in vivo formulations just described, the polymeric carrier particles of the present invention may be incorporated in a wide variety of formulations for in vitro use. Such formulations include air freshener compositions, disinfectant compositions, bacteriostats, and the like.

The following experimental results are offered by way of illustration, not by way of limitation.

The following examples are offered by way of illustration, not by way of limitation.

EXPERIMENTAL

Materials and Methods

Example 1—One Step Entrapment of Preformed Linear Polymer

Macroporous polymer beads (35.87 g) were prepared by suspension copolymerization of methyl methacrylate and ethyleneglycoldimethacrylate generally as described in U.S. Pat. No. 4,806,360, Example 2. After porogen extraction, the beads were loaded with 10% w/w D&C Red #28 and were placed in a crystallizing dish. A solution consisting of poly(methylmethacrylate-comethacrylic acid) (1.81 g; Eudragit S100 from Röhm Pharma GmbH, Darmstadt, West Germany) and 70 mL isopropanol was slowly added to the polymer with constant stirring. The dish was then warmed on a hot plate and stirred while enough additional isopropanol was added to result in a thin slurry. The isopropanol was allowed to evaporate while being stirred until the material was in the form of a powder. The sample was then dried in a vacuum oven at 79° C. overnight.

Example 2—Two Step Entrapment of Preformed Linear Polymer

The procedure outlined in Example 1 is followed except that the only isopropanol added is that which contained the Eudragit. After evaporation of the isopropanol, a somewhat chunky product results. The clumps are broken apart by placing the sample (polymer+D&C Red #2+Eudragit S100) into a 500 mL resin kettle fitted with a reflux condenser and twin turbine stirrer. Mineral spirits is added in the ratio of 12:1 mineral spirits:sample. Stirring is then started at 800 rpm and the reaction is heated to reflux. The heat is turned off after having refluxed for 30 minutes and the material is allowed to slowly cool to room temperature while still being stirred. When cooled to room temperature the material is filtered, washed 2× with heptane (mineral spirits:heptane ratio of 2:1) and then dried overnight, under vacuum at 79° C.

Example 3—One Step Polymerization of Entrapped Monomers

A solution of 1.01 g D&C Red #28, 0.28 g ethyleneglycol dimethacrylate, 1.42 g water, 9.91 g hydroxyethyl methacrylate, and 0.02 g azobis(isobutyronitrile) was combined and deoxygenated by a nitrogen purge. This solution was slowly poured onto 9 g of blank styrene/divinylbenzene beads (prepared generally as described in U.S. Pat. No. 4,806,360, Example 1, with a pore volume of 1.54 cc/g) with stirring. The loaded sponges were them polymerized under an inert atmosphere for 8 hours at 70° C. The beads were then washed with 100 mL of THF to remove unreacted monomers and then dried overnight at 50° C. under vacuum.

Example 4—Two Step Polymerization of Entrapped Monomers

The loading procedure and amounts from Example 3 are used. A 100 mL resin kettle is fitted with nitrogen inlet, oil bath, and paddle stirrer. A solution of 0.15 octadecyl vinyl ether/maleic anhydride copolymer in 60 mL mineral spirits is then added. The monomer-loaded beads are then placed into the resin kettle, stirring is started at 300 rpm, and an inert atmosphere is established. The reaction is heated to 70° C. and maintained at this temperature for 8 hours. The beads are then separated by filtration, washed 2×100 mL with THF, and then dried overnight at 79° C. under vacuum.

Particle Size Determination

The particle size determinations were conducted using a Particle Sizer 3600 E Type (Malvern Instruments, Malvern, England).

In Vitro Release

The in vitro release of D&C Red #28 from the loaded beads was studied using Dissolution Apparatus I described in USP XXII with a dissolution basket made of five micron screen cloth. Approximately 100 mg of polymer was put into each individual basket. The samples were then wetted in each basket and lowered into 500 ml of their respective dissolution mediums. The dissolution mediums were buffer solutions at pH 3, 5.5, and 8 composed from citric acid and disodium phosphate with 0.5% sodium lauryl sulfate as a surfactant. The dissolution mediums were maintained at 22° C. and kept covered throughout the experiment. The stirring speed was set at 150 rpm. The cumulative release of D&C Red #28 was determined by analyzing the samples of the dissolution medium collected at predetermined time intervals for D&C Red #28 content by spectrophotometric analysis at 538 nm.

Results

Table 1 illustrates that even after loading the beads with D&C Red #28 and then impregnating with Eudragit RS100 (loading levels of 5%, 10% and 15%) there was no significant increase in the particle size of the beads.

TABLE 1

|  | Particle Size (wt %) | Dispersion (%) |
|---|---|---|
| Blank Polymer | 17.04 | 2.7 |
| Polymer + D&C Red #28 | 27.86 | 4.8 |
| Polymer + D&C Red #28 + 5% Eudragit | 27.51 | 4.5 |
| Polymer + D&C Red #28 + 10% Eudragit | 21.90 | 3.8 |
| Polymer + D&C Red #28 + 15% Eudragit | 18.65 | 2.4 |

Controlled Release of Soluble Active from Loaded Beads

FIG. 1 illustrates the release of D&C Red #28 from beads impregnated with 5% Eudragits RS-100 and RL-100 compared to beads with no eudragit into distilled water. There does not appear to be a noticeable difference in release of D&C Red #28 from beads impregnated with Eudragits RS-100 and RL-100, but significant difference in comparison to beads with no eudragit.

Figure 2:
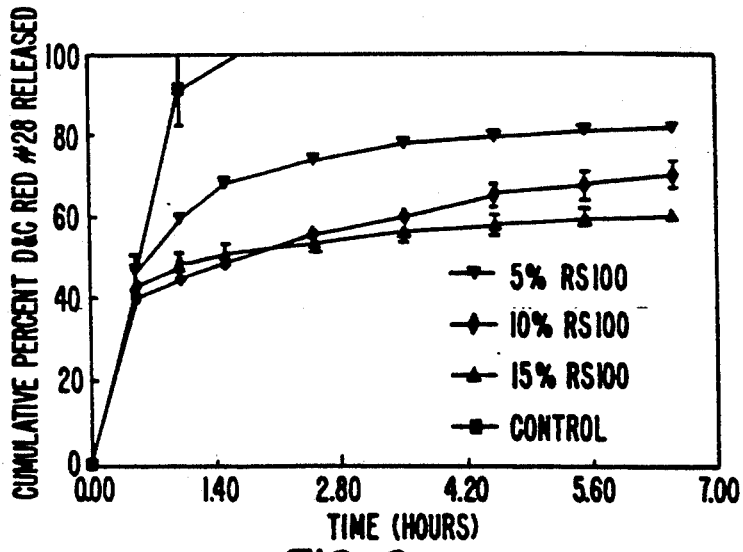
FIG. 2 is a graph which compares release rates of a dye from polymeric particles blocked with different amounts of a Eudragit compound.

FIG. 2 shows the release of D&C Red #28 from loaded beads as a function of 5%, 10% and 15% Eudragit RS-100 loading. The polymer impregnated with 5% Eudragit has a faster release than that with 10% Eudragit. Beads with 15% Eudragit impregnation shows the slowest release of dye of the three impregnations compared. The release profile was dependent on the percent Eudragit, with the higher Eudragit loading causing a slower release profile.

pH Triggered Controlled Release of Soluble Actives from Beads

Figure 3:
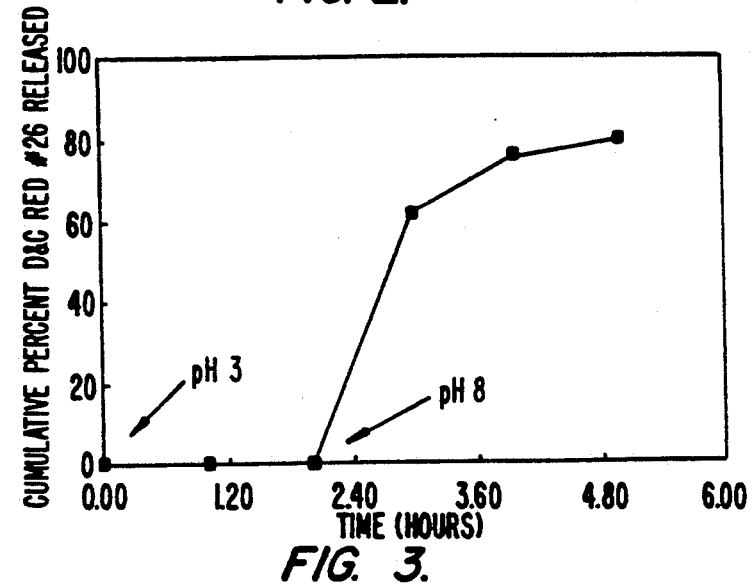
FIG. 3 is a graph which illustrates the effect of pH change on the release rate of a dye from polymeric particles blocked with a pH-sensitive Eudragit combination.

FIG. 3 illustrates the release of D&C Red #28 from beads impregnated with a 5% pH independent and 5% pH dependent polymers (Eudragit RS-100, S-100). An undetectable amount of D&C Red #28 was released at pH 3 for about a period of 2 hours. When the pH of the dissolution medium was changed to pH 8, the release was triggered and 80% of the D&C Red #28 was released over a period of 3 hours.

To deliver soluble actives at a controlled rate from topical formulations, a polymeric particle delivery system was loaded with D&C Red #28 (model compound) and then impregnated with pH dependent and/or pH independent Eudragits. This impregnation did not significantly alter the particle size. The in vitro release of D&C Red #28 from these systems showed that the release could be triggered by a change in the pH of the immediate environment by using pH dependent Eudragits and the release rate could be controlled by changing the percent loading of pH independent Eudragits. From these studies it is evident that the release of active substances entrapped in the polymeric particle delivery system can be triggered by a change in pH of the immediate environment and then delivered at a controlled rate.

Although the foregoing invention has been described in detail for purposes of clarity of understanding, it will be obvious that certain modifications may be practiced within the scope of the appended claims.

What is claimed is:

1. A composition for the controlled release of an active substance, said composition comprising polymeric particles present in a liquid carrier non-degrading to said polymeric particles, wherein the polymeric particles each define a network of internal pores having therein (1) the active substance and (2) a blocking agent having physical and chemical characteristics selected to degrade and release the active substance from the internal pores in response to changes in external conditions and wherein the liquid carrier is selected to inhibit degradation of the blocking agent to maintain the active substance within the pores, wherein the blocking agent is selected from the group consisting of polymeric and non-polymeric enterosoluble materials.

2. A composition as in claim 1, wherein the polymeric particles are substantially non-collapsible.

3. A composition as in claim 2, wherein said polymeric particles are composed of a copolymer selected from the group consisting of styrene-divinylbenzene, methacrylate-ethylene glycol dimethacrylate, vinyl stearate-divinylbenzene, 4-vinylpyridine-ethylene glycol dimethacrylate, and 4-vinylpyridine-divinylbenzene.

4. A composition as in claim 2, wherein said polymeric particles are substantially spherical in shape and have an average diameter of about 1 micron to about 100 microns, a total pore volume of about 0.01 cc/g to about 4.0 cc/g, an average surface area of about 2 $m^2/g$ to 500 $m^2/g$, an average pore diameter of about 0.001 micron to about 3.0 microns, and a cross-linking density of at least about 20%.

5. A composition as in claim 1, wherein the active substance is a solid and wherein the polymeric particles are present in a vehicle which is a solvent for the active substance.

6. A composition as in claim 5, wherein the active substance is a liquid, gel, or semi-solid.

7. A composition as in claim 1, wherein the active substance is selected from the group consisting of analgesics, anesthetics, antihelminthics, antidotes, antiemitics, antihistamines, antimalarials, antipyretics, antiseptics, antituberculotics, antitussives, antivirals, cardioactive drugs, cathartics, chemotherapeutic agents, corticosteroids, diagnostic aids, diuretics, enzymes, expectorants, hormones, hypnotics, nutritional supplements, parasympathomimetics, potassium supplements, sedatives, sulfonamides, stimulants, sympathomimetics, tranquilizers, urinary antiinfectives, vasoconstrictors, and vasodilators.

8. A composition as in claim 1, wherein the blocking agent is a liner polymer.

9. A composition as in claim 1, wherein the blocking agent is a cross-linked copolymer.

10. A composition as in claim 8, wherein the blocking agent is selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer.

11. A composition as in claim 1, wherein the blocking agent is selected from the group consisting of fat-fatty acid mixtures, ethyl cellulose, and cellulose acetate phthalates.

12. A composition as in claim 1, wherein the blocking agent is pH labile and the liquid carrier has a pH which allows the blocking agent to remain stable.

13. A method for preparing a controlled release composition, said method comprising performing the following steps in a predetermined order:
(a) introducing an active substance into a network of internal pores formed in polymeric particles;
(b) introducing a blocking agent into the network of internal pores, said blocking agent having physical and chemical characteristics selected to degrade and release the active substance from the internal pores in response to changes in external conditions, wherein the blocking agent is selected from the group consisting of polymeric and non-polymeric enterosoluble materials; and
incorporating the polymeric particles in a liquid carrier non-degrading to said polymeric particles which is selected to inhibit degradation of the blocking agent.

14. A method as in claim 13, wherein the active substance is introduced prior to introducing the blocking agent material.

15. A method as in claim 13, wherein the blocking agent is introduced prior to introducing the active substance.

16. A method as in claim 13, wherein the active substance and the blocking agent are introduced simultaneously.

17. A method as in claim 13, wherein the active substance is introduced by absorption.

18. A method as in claim 13, wherein the blocking agent is introduced by in situ polymerization of monomers.

19. A method as in claim 13, wherein the blocking agent is a preformed polymer introduced by absorption.

20. A method as in claim 13, wherein the polymeric particles are substantially non-collapsible.

21. A method as in claim 20, wherein said polymeric particles are composed of a copolymer selected from the group consisting of styrene-divinylbenzene, methacrylate-ethylene glycol dimethacrylate, vinyl stearate-divinylbenzene, 4-vinylpyridine-ethylene glycol dimethacrylate, and 4-vinylpyridine-divinylbenzene.

22. A composition as in claim 20, wherein said polymeric particles are substantially spherical in shape and have an average diameter of about 1 micron to about 100 microns, a total pore volume of about 0.01 cc/g to about 4.0 cc/g, an average surface area of about 2 $m^2/g$ to 500 $m^2/g$, an average pore diameter of about 0.001 micron to about 3.0 microns, and a cross-linking density of at least about 20%.

23. A composition as in claim 13, wherein the active substance is a solid and wherein the polymeric particles are present in a vehicle which is a solvent for the active substance.

24. A composition as in claim 13, wherein the active substance is a liquid, gel, or semi-solid.

25. A method as in claim 13, wherein the active substance is selected from the group consisting of analgesics, anesthetics, antihelminthics, antidotes, antiemitics, antihistamines, antimalarials, antipyretics, antiseptics, antituberculotics, antitussives, antivirals, cardioactive drugs, cathartics, chemotherapeutic agents, corticosteroids, diagnostic aids, diuretics, enzymes, expectorants, hormones, hypnotics, nutritional supplements, parasympathomimetics, potassium supplements, sedatives, sulfonamides, stimulants, sympathomimetics, tranquilizers, urinary antiinfectives, vasoconstrictors, and vasodilators.

26. A method as in claim 13, wherein the blocking agent is a polymeric material.

27. A method as in claim 26, wherein the blocking agent is a linear polymer.

28. A composition as in claim 27, wherein the blocking agent is selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer.

29. A method as in claim 26, wherein the blocking agent is a cross-linked copolymer.

30. A method as in claim 13, wherein the blocking agent is an enterosoluble material selected from the group consisting of fat-fatty acid mixtures, ethyl cellulose, and cellulose acetate phthalates.

31. A method for delivering an active substance to a preselected environment, said method comprising introducing to said environment a composition of polymeric particles present in a liquid carrier non-degrading to said polymeric particles, wherein the polymeric particles each define a network of internal pores having there (1) the active substance and (2) a blocking agent having physical and chemical characteristics selected to degrade and release the active substance from the internal pores in response to changes in external conditions and wherein the liquid carrier is selected to inhibit degradation of the blocking agent to maintain the active substance within the pores, wherein the blocking agent is selected from the group consisting of polymeric and non-polymeric enterosoluble materials, whereby introduction of the particles to the environment permits degradation of the blocking agent and release of the active substance.

32. A method for delivering as in claim 30, wherein the preselected environment is at a first pH and the carrier is at a second pH and wherein the blocking agent is selected to inhibit release of the active substance at said second pH and allow release of the active substances at said first pH.

33. A method as in claim 31, wherein the polymeric particles are substantially non-collapsible.

34. A method as in claim 33, wherein said polymeric particles are composed of a copolymer selected from the group consisting of styrene-divinylbenzene, methacrylate-ethylene glycol dimethacrylate, vinyl stearate-divinylbenzene, 4-vinylpyridine-ethylene glycol dimethacrylate, and 4-vinylpyridine-divinylbenzene.

35. A composition as in claim 33, wherein said polymeric particles are substantially spherical in shape and have an average diameter of about 1 micron to about 100 microns, a total pore volume of about 0.01 cc/g to about 4.0 cc/g, an average surface area of about 2 $m^2$/g to 500 $m^2$/g, an average pore diameter of about 0.001 micron to about 3.0 microns, and a cross-linking density of at least about 20%.

36. A method as in claim 31, wherein the active substance is a solid and wherein the polymeric particles are present in a vehicle which is a solvent for the active substance.

37. A method as in claim 36, wherein the active substance is a liquid, gel, or semi-solid.

38. A method as in claim 31, wherein the active substance is selected from the group consisting of analgesics, anesthetics, antihelminthics, antidotes, antiemitics, antihistamines, antimalarials, antipyretics, antiseptics, antituberculotics, antitussives, antivirals, cardioactive drugs, cathartics, chemotherapeutic agents, corticosteroids, diagnostic aids, diuretics, enzymes, expectorants, hormones, hypnotics, nutritional supplements, parasympathomimetics, potassium supplements, sedatives, sulfonamides, stimulants, sympathomimetics, tranquilizers, urinary antiinfectives, vasoconstrictors, and vasodilators.

39. A method as in claim 31, wherein the blocking agent is a polymeric material.

40. A method as in claim 39, wherein the blocking agent is a linear polymer.

41. A method as in claim 39, wherein the blocking agent is a cross-linked copolymer.

42. A method as in claim 40, wherein the blocking agent is selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer.

43. A method as in claim 31, wherein the blocking agent is an enterosoluble material selected from the group consisting of fat-fatty acid mixtures, ethyl cellulose, and cellulose acetate phthalates.

44. A composition for the controlled release of an active substance, said composition comprising polymeric particles present in a liquid carrier, wherein the polymeric particles each define a network of internal pores having therein (1) the active substance;

(2) a blocking agent having physical and chemical characteristics selected to degrade and release the active substance from the internal pores in response to changes in external conditions, wherein the blocking agent is a cross-linked co-polymer material selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer; and wherein the liquid carrier is selected to inhibit degradation of the blocking agent to maintain the active substance within the pores.

45. A composition for the controlled release of an active substance, said composition comprising polymeric particles present in a liquid carrier, wherein the polymeric particles each define a network of internal pores having therein (1) the active substance;

(2) a blocking agent having physical and chemical characteristics selected to degrade and release the active substance from the internal pores in response to changes in external conditions, wherein the blocking agent is an enterosoluble material selected from the group consisting of fat-fatty acid mixtures, ethyl cellulose, and cellulose acetate phthalates; and wherein the liquid carrier is selected to inhibit degradation of the blocking agent to maintain the active substance within the pores.

46. A method for preparing a controlled release composition, said method comprising performing the following steps in a predetermined order:

(a) introducing an active substance into a network of internal pores formed in polymeric particles;

(b) introducing a blocking agent into the network of internal pores, said blocking agent having physical and chemical characteristics selected to degrade and release the active substance from the internal pores in response to changes in external conditions, wherein the blocking agent is a preformed polymer introduced by absorption; and (c) incorporating the polymeric particles in a liquid carrier which is selected to inhibit degradation of the blocking agent.

47. A method for preparing a controlled release composition, said method comprising performing the following steps in a predetermined order:

(a) introducing an active substance into a network of internal pores formed in polymeric particles, wherein the active substance is a liquid, gel, or semi-solid;

(b) introducing a blocking agent into the network of internal pores, said blocking agent having physical and chemical characteristics selected to degrade and release the active substance from the internal pores in response to changes in external conditions, wherein the blocking agent is a polymeric enterosoluble material; and (c) incorporating the polymeric particles in a liquid carrier which is selected to inhibit degradation of the blocking agent.

48. A method for preparing a controlled release composition, said method comprising performing the following steps in a predetermined order:
  (a) introducing an active substance into a network of internal pores formed in polymeric particles; and
  (b) introducing a blocking agent into the network of internal pores, said blocking agent having physical and chemical characteristics selected to degrade and release the active substance from the internal pores in response to changes in external conditions, wherein the blocking agent is a cross-linked copolymer material selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer; and
  (c) incorporating the polymeric particles in a liquid carrier which is selected to inhibit degradation of the blocking agent.

49. A method for preparing a controlled release composition, said method comprising performing the following steps in a predetermined order:
  (a) introducing an active substance into a network of internal pores formed in polymeric particles;
  (b) introducing a blocking agent into the network of internal pores, said blocking agent having physical and chemical characteristics selected to degrade and release the active substance from the internal pores in response to changes in external conditions, wherein the blocking agent is an enterosoluble material selected from the group consisting of fat-fatty acid mixtures, ethyl cellulose, and cellulose acetate phthalates; and
  (c) incorporating the polymeric particles in a liquid carrier which is selected to inhibit degradation of the blocking agent.

50. A method for delivering an active substance to a preselected environment, said method comprising introducing to said environment a composition comprising polymeric particles present in a liquid carrier, wherein the polymeric particles each define a network of internal pores having therein
  (1) the active substance, and
  (2) a blocking agent in to the network of internal pores, said blocking agent having physical and chemical characteristics selected to degrade and release the active substance from the internal pores in response to changes in external conditions, wherein the blocking agent is a cross-linked copolymer material selected from the group consisting of: poly(methacrylic acid, ethylacrylate) copolymer, poly(methacrylic acid, methylmethacrylate) copolymer, poly(ethylacrylate, methylmethacrylate) copolymer, poly(ethylacrylate, methacrylic acid) trimethylammoniumethylmethacrylate chloride copolymer, and poly(ethylacrylate, methylmethacrylate) trimethylammoniumethylmethacrylate chloride copolymer; and
  wherein the liquid carrier is selected to inhibit degradation of the blocking agent to maintain the active substance within the pores.

51. A method for delivering an active substance to a preselected environment, said method comprising introducing to said environment a composition comprising polymeric particles present in a liquid carrier, wherein the polymeric particles each define a network or internal pores having therein
  (1) the active substance, and
  (2) a blocking agent having physical and chemical characteristics selected to degrade and release the active substance from the internal pores in response to changes in external conditions, wherein the blocking agent is an enterosoluble material selected from the group consisting of fat-fatty acid mixtures, ethyl cellulose, and cellulose acetate phthalates; and
  wherein the liquid carrier is selected to inhibit degradation of the blocking agent to maintain the active substance within the pores.

* * * * *